(12) United States Patent
Suuronen

(10) Patent No.: US 6,628,753 B2
(45) Date of Patent: Sep. 30, 2003

(54) X-RAY IMAGING APPARATUS

(75) Inventor: Esa Suuronen, Kerava (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 10/039,133

(22) Filed: Jan. 2, 2002

(65) Prior Publication Data

US 2002/0106053 A1 Aug. 8, 2002

(30) Foreign Application Priority Data

Jan. 5, 2001 (FI) .............................................. 20010015

(51) Int. Cl.[7] .................................................. G21K 1/02
(52) U.S. Cl. ....................................................... 378/147
(58) Field of Search ............................. 378/38, 39, 40, 378/57, 64, 65, 119, 121, 145, 146, 147, 148–153, 167, 177, 178, 154–155, 4–19, 137–138, 113–116

(56) References Cited

U.S. PATENT DOCUMENTS

| | | | |
|---|---|---|---|
| 4,165,461 A | | 8/1979 | Ishijima |
| 4,998,270 A | * | 3/1991 | Scheid et al. ................ 378/155 |
| 5,070,519 A | * | 12/1991 | Stein et al. ................ 378/146 |
| 5,436,950 A | | 7/1995 | Pauli et al. |
| 5,511,106 A | | 4/1996 | Doebert et al. |
| 5,550,886 A | | 8/1996 | Dobbs et al. |
| 5,600,700 A | * | 2/1997 | Krug et al. .................... 378/57 |
| 5,651,043 A | * | 7/1997 | Tsuyuki et al. ................ 378/65 |
| 5,974,111 A | * | 10/1999 | Krug et al. .................... 378/57 |
| 6,094,469 A | | 7/2000 | Dobbs et al. |

\* cited by examiner

Primary Examiner—William Oen
(74) Attorney, Agent, or Firm—Andrus, Sceales, Starke & Sawall, LLP

(57) ABSTRACT

The invention relates to an apparatus for X-ray imaging, in which imaging an X-ray beam (11) is directed through the object being imaged. The X-ray imaging apparatus (1) comprises an X-ray source (5) in front of the object being imaged, a primary collimator (6) in conjunction with the X-ray source, and radiation receiving means (15), which are located in a position behind the object being imaged. The apparatus relating to the invention comprises identifying means (20–22) which react to X-ray radiation, by means of which is ensured the entry of radiation inside the imaging area of the radiation receiving means (15).

8 Claims, 3 Drawing Sheets

Figure 3:
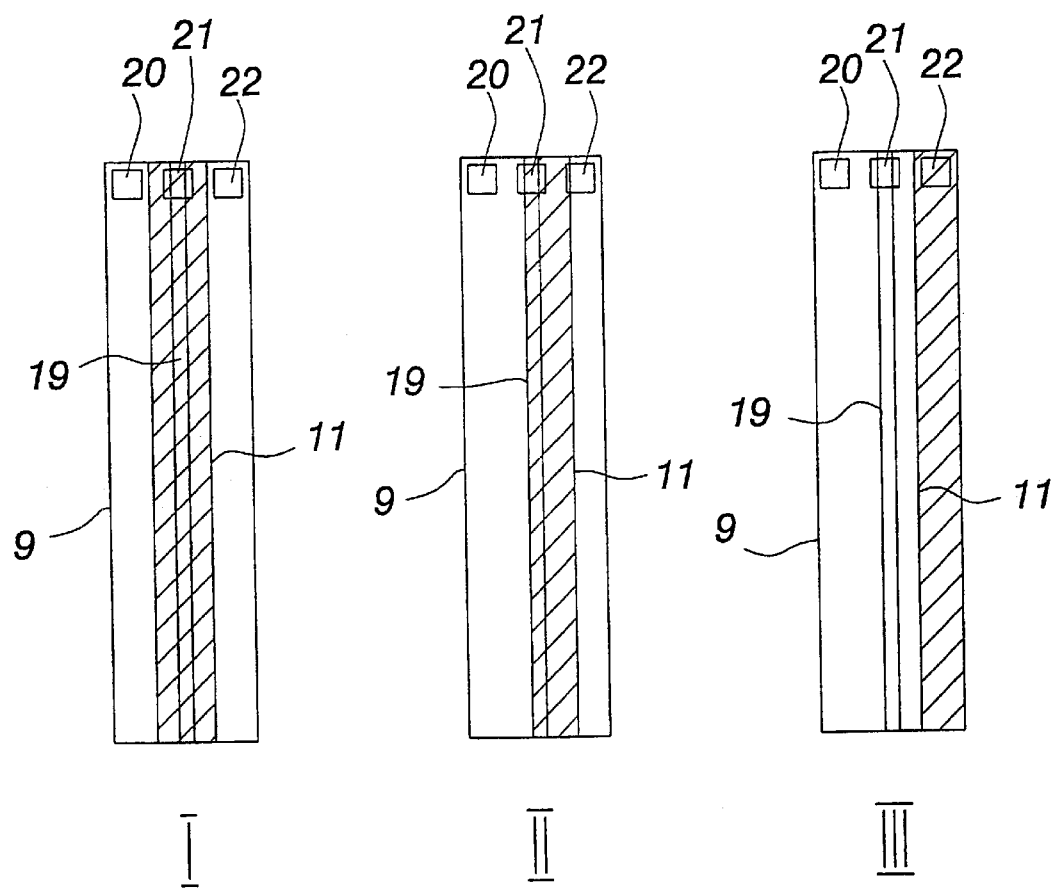

X-RAY IMAGING APPARATUS

CROSS REFERENCE TO RELATED APPLICATION

The present application claims priority of Finnish Patent Application 20010015, filed Jan. 5, 2001.

SUMMARY OF THE INVENTION

The present invention relates to an X-ray imaging apparatus for carrying out scanning x-ray imaging, the X-ray imaging apparatus comprising:

an X-ray source in front of the object being imaged for generating X-ray radiation, a primary collimator for forming an X-ray beam of the X-ray radiation generated and for directing the X-ray beam through the object being imaged, and X-ray radiation receiving means located behind the object being imaged for receiving X-ray radiation.

BACKGROUND OF THE INVENTION

The invention is intended for use in X-ray imaging in general, where the radiation receiving means are not in fixed mechanical contact with the radiation source. The invention is applicable, for example, to intraoral imaging, scanning cephalometric imaging, and so-called still imaging. In scanning cephalometric imaging, an X-ray beam located substantially on the vertical plane is directed from the X-ray source through the object being imaged, and the X-ray source is at the same time turned about the rotation centre located between the X-ray source and the line detector camera in order to scan the object being imaged in the horizontal direction, whereby the line detector camera is moved during the scanning movement in such a way that the ray beam meets the vertical slot of the line detector camera. The publication U.S. Pat. No. 5,511,106 discloses this type of scanning cephalometric imaging method. The earlier Finnish patent application FI 20000369 by the applicant of the present application discloses a scanning cephalometric imaging method, in which the effective focal spot of the X-ray source is transferred from the rotation centre to the focal spot of the X-ray source by transferring the rotation centre by means of a transverse linear movement with respect to the ray beam. In still imaging, the imaging is carried out on the whole object to be imaged at once.

When cephalometric imaging is carried out according to the method relating to the application FI 20000369, manufacturing tolerances, for example, may cause the ray beam to move at a different speed or in incorrect alignment with respect to the collimator or detector, in which case there is a risk of the radiation being incorrectly aligned, that is, the ray beam does not meet the active imaging area of the imaging detector, thus necessitating a retake and possibly exposing a patient or personnel unnecessarily to radiation. Furthermore, the movements are only linked with each other programmatically, which means that a possible error in the control electronics may also result in incorrect alignment of the radiation. Correspondingly, also in other methods of X-ray imaging, where there is no fixed mechanical connection between the X-ray source and the radiation receiving means, similar incorrect alignment of radiation may occur.

Accordingly, one important aim of the present invention is to provide an X-ray imaging apparatus, by means of which the above-mentioned disadvantages can be eliminated. To achieve this aim, the X-ray imaging apparatus relating to the invention is characterised in that the X-ray imaging apparatus comprises X-ray radiation identifying means for producing a control signal, on the basis of which control signal the position of the X-ray beam emitted from the X-ray source with respect to the X-ray radiation receiving means can be located and, if necessary, the ray beam can be directed inside the imaging area of the radiation receiving means, and on the basis of which control signal the movements of the apparatus required by scanning imaging can be adjusted so as to be synchronised with each other.

If necessary, the apparatus relating to the invention can also be used to help in directing radiation to the imaging detector, for example, in still imaging.

BRIEF DESCRIPTION OF THE DRAWINGS

The invention is described in greater detail in the following, with reference to the accompanying drawings, in which FIG. 1 shows a diagrammatic top view of an embodiment relating to the invention, when applied to cephalometric imaging, FIG. 2 shows diagrammatically a view in principle of the line detector camera used in the apparatus according to FIG. 1, FIG. 3 shows diagrammatically the mutual positions of the radiation beam and the identifying means comprised in the apparatus relating to the invention in different situations.

DETAILED DESCRIPTION OF THE INVENTION

The apparatus according to FIG. 1 comprises a support part 2, beneath which is connected a panoramic imaging apparatus 4, which turns in a pivoting manner around the rotation centre 13, the imaging apparatus comprising a C arm 7, on one vertical branch **7*a* of which is arranged an X-ray source 5 and the primary collimator 6 in its vicinity. To the support part 2 is connected a supporting arm 3, at the other end of which is the cephalometric imaging apparatus 10, which comprises a line detector camera 8 to be placed behind the object being imaged, and a secondary collimator 9** to be placed in front of the object being imaged.

FIG. 2 shows diagrammatically one implementation of a line detector camera 8, wherein on one side of the camera is formed a slot 14, behind which, inside the camera 8, is a digital detector 15, for example, a CCD sensor comprising several pixels. The active imaging area of the detector 15 consists of areas 15A and 15B, of which 15A represents the area which the ray beam must meet in a normal situation. In cephalometric imaging, the patient's head is scanned by means of a vertically positioned ray beam 11 from right to left or vice versa by turning the X-ray source 5 about the rotation centre 13, whereby the ray beam 11 is directed at the detector 15 behind the substantially vertical slot 14 of the line detector camera 8, from which detector 15 the image data is transmitted further, for example, to a microprocessor. According to the FI application no. 20000369, the rotation centre 13 is arranged to be transferred by means of a linear movement, transversely with respect to the ray beam 11, as shown by reference marking A in FIG. 1.

In the embodiment shown in FIG. 1, the apparatus is further provided with three identifying detectors 20–22 on that surface of the secondary collimator 9, which is on the X-ray source 5 side, of which the middlemost identifying detector 21 is located preferably at the slot 19 of the secondary collimator 9. In the embodiment shown, the identifying detectors are located according to FIG. 3 in the upper part of the secondary collimator, but they may also be located elsewhere on the said surface or outside it. There may obviously also be only one or two or more than three identifying means, depending on the amount of information desired.

FIG. 3 depicts a situation at stage I, where the middlemost identifying detector 21 is in the ray beam and the outer identifying detectors are outside it. In such a case, the ray beam 11 moves synchronically with the secondary collimator, and the radiation is directed correctly at the imaging detector, which means that no corrective movements are required. Stage II depicts a situation, where the ray beam 11 meets partly both the middlemost identifying detector 21 and the outer detector 22, whereby the ray beam 11 and the secondary collimator 9 move at different speeds and a corrective movement is required to bring them back to the synchronised movement according to stage I. For this purpose, the identifying detectors transmit signals by means of which the movements are guided in a desired direction, for example, a fast movement is slowed down. Stage III depicts a situation, where the corrective movement has not given the desired end result, but the middlemost identifying detector 21 has moved completely outside the ray beam 11, whereby the radiation is no longer directed at the imaging area of the imaging detector 15 at all. In such a case, the signals transmitted by the identifying detectors are preferably used to discontinue exposure to avoid unnecessary irradiation.

Figure 1:
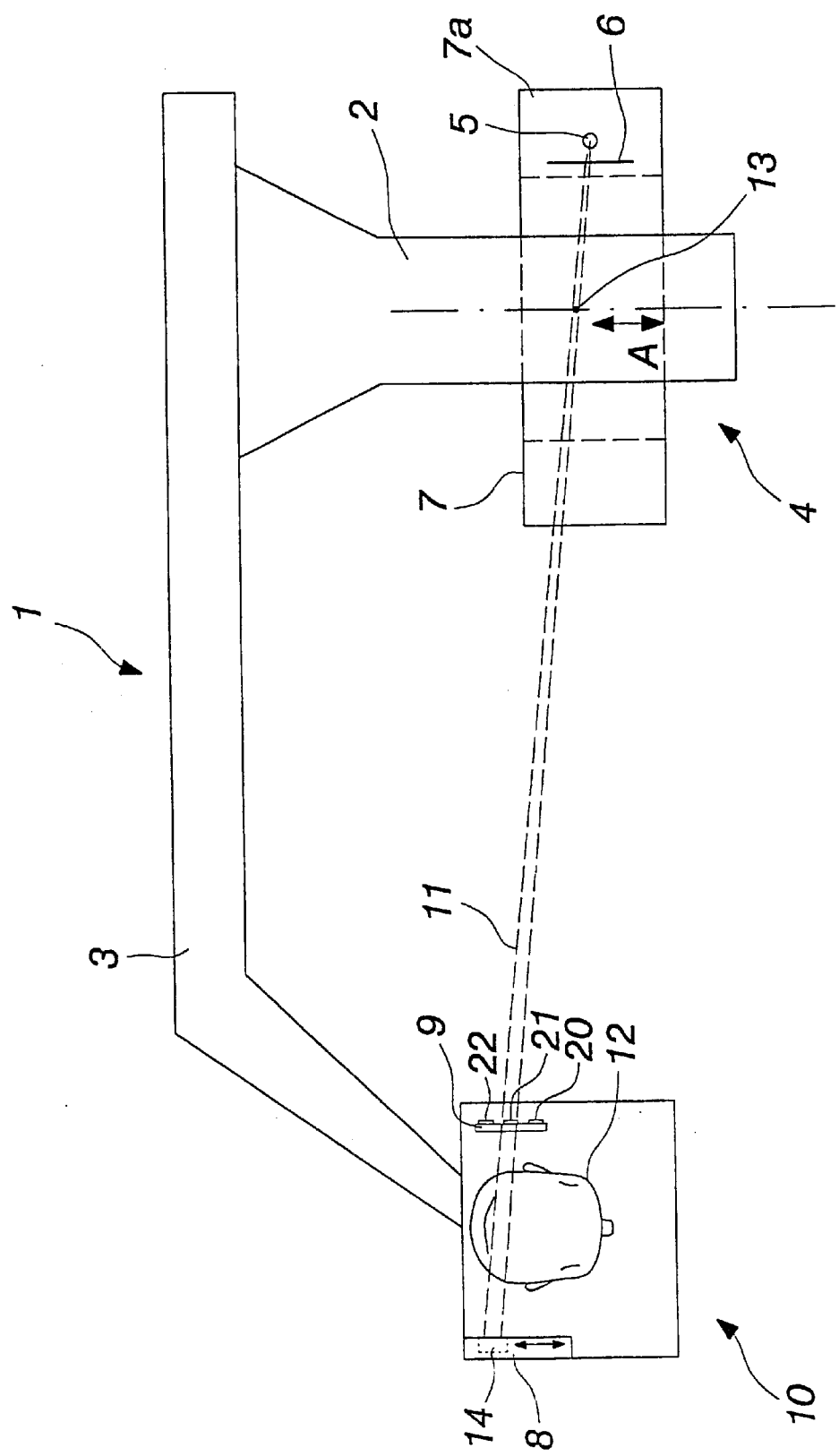
Figure 2:
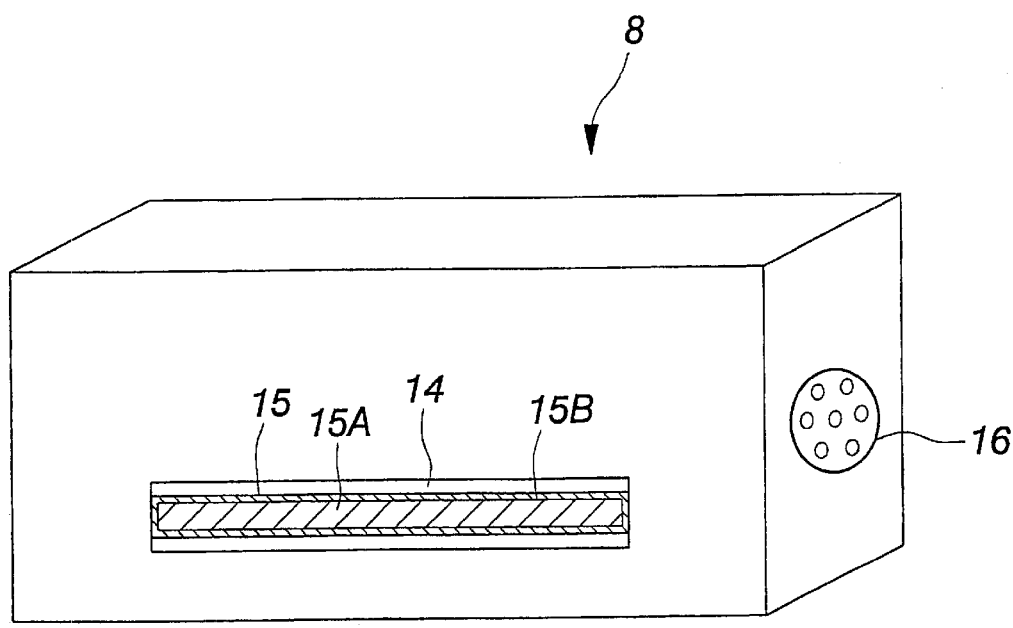

The identifying detectors are preferably located in conjunction with the secondary collimator, but they may also be located elsewhere, for example, in connection with the imaging detector 15, or the imaging detector itself can be used as an identifying detector, for example, by using, as the pixels forming the identifying detector, the pixels in such an area (area 15B in FIG. 2) of the active imaging area of the imaging detector, which are not irradiated in a normal situation, and which give out an identifying signal if radiation is directed at them. Alternatively, can also be used such pixels (in area 15A in FIG. 2) located inside the active imaging area, which are normally arranged to be in the field of rays and to give information on the radiation meeting the detector. The necessary corrective movements are made or the exposure is discontinued on the basis of the information received from the detector. Using the imaging detector as an identifying detector or locating identifying detectors in connection with it is more disadvantageous than using identifying detectors located in front of the secondary collimator in the respect that any corrective movements or discontinuance of exposure are based on radiation that has passed through the patient, whereby radiation scattered from the patient may cause unclear situations and unnecessary corrective movements or discontinuance of exposure. Furthermore, in a situation where exposure is discontinued, the patient is exposed to more radiation than in a situation where the identifying detectors are located in conjunction with the secondary collimator or in another part of the imaging apparatus in front of them.

What is claimed is:

1. An X-ray imaging apparatus for carrying out scanning X-ray imaging, the X-ray imaging apparatus comprising:
   an X-ray source (5) in front of the object being imaged for generating X-ray radiation,
   a primary collimator (6) for forming an X-ray beam (11) of the X-ray radiation generated and for directing the X-ray beam through the object being imaged, and
   X-ray radiation receiving means (15) located behind the object being imaged for receiving X-ray radiation, characterised in that the X-ray imaging apparatus comprises X-ray radiation identifying means (20–22) for producing a control signal, on the basis of which control signal, the position of the X-ray beam emitted from the X-ray source (5) with respect to the X-ray radiation receiving means (15) can be located and, if necessary, the ray beam can be directed inside the imaging area of the radiation receiving means and on the basis of which control signal, the movements of the apparatus required by scanning imaging can be adjusted so as to be synchronised with each other.

2. An apparatus as claimed in claim 1, characterised in that the radiation receiving means comprise a digital imaging detector (15).

3. An apparatus as claimed in claim 1, characterised in that the apparatus is used as scanning cephalometric imaging apparatus, which comprises a line detector camera (8) equipped with a digital imaging detector (15) and a secondary collimator (9) in the vicinity of the line detector camera (8), and that the identifying means (20–22) produce a control signal by means of which the movements of the apparatus required by scanning cephalometric imaging are mutually synchronised and/or maintained synchronised.

4. An apparatus as claimed in claim 3, characterised in that as identifying means is used at least one identifying detector (20–22) located on that surface of the secondary collimator (9), which is on the X-ray source (5) side.

5. An apparatus as claimed in claim 4, characterised in that the said at least one identifying detector is located at the slot (19) of the secondary collimator (9).

6. An apparatus as claimed in claim 1, characterised in that as the apparatus is used an intraoral imaging apparatus.

7. An apparatus as claimed in claim 1, wherein the radiation receiving means is a digital imaging detector, characterised in that as identifying means are used such pixels inside (15B) the active imaging area of the imaging detector (15), which are normally arranged to be radiation-free and to give out an identifying signal when radiation meets them.

8. An apparatus as claimed in claim 1, wherein the radiation receiving means is a digital imaging detector, characterised in that as identifying means are used such pixels inside (15A) the active imaging area of the imaging detector (15), which are normally arranged to be in the field of rays and to provide information on radiation meeting the detector.

* * * * *